(12) United States Patent
Brown et al.

(10) Patent No.: US 9,976,995 B2
(45) Date of Patent: May 22, 2018

(54) STAGGERED CHROMATOGRAPHY MASS SPECTROMETRY

(71) Applicant: Micromass UK Limited, Wilmslow (GB)

(72) Inventors: Jeffery Brown, Hyde (GB); Steven Foster, Altrincham (GB)

(73) Assignee: Micromass UK Limited, Wilmslow (GB)

( * ) Notice: Subject to any disclaimer, the term of this patent is extended or adjusted under 35 U.S.C. 154(b) by 0 days. days.

(21) Appl. No.: 15/317,295

(22) PCT Filed: Jun. 12, 2015

(86) PCT No.: PCT/GB2015/000177
§ 371 (c)(1),
(2) Date: Dec. 8, 2016

(87) PCT Pub. No.: WO2015/189549
PCT Pub. Date: Dec. 17, 2015

(65) Prior Publication Data
US 2017/0138915 A1    May 18, 2017

(30) Foreign Application Priority Data

Jun. 12, 2014 (GB) .................................. 1410521.7

(51) Int. Cl.
*H01J 49/26* (2006.01)
*G01N 30/72* (2006.01)
*G01N 30/62* (2006.01)

(52) U.S. Cl.
CPC ......... *G01N 30/7233* (2013.01); *G01N 30/62* (2013.01)

(58) Field of Classification Search
CPC ............... G01N 30/7233; G01N 30/62; G01N 30/7213; H01J 49/00; H01J 49/0027;
(Continued)

(56) References Cited

U.S. PATENT DOCUMENTS 4,057,997 A * 11/1977 Chandler ............... G01N 30/06
73/23.41
7,797,988 B2   9/2010 Schultz et al.
(Continued)

OTHER PUBLICATIONS

Yates, J. et al., "*Proteomics by Mass Spectrometry: Approaches, Advances, and Applications*", Annual Review of Biomedical Engineering, vol. 11, No. 1, pp. 49-70, (Aug. 2009).

*Primary Examiner* — Nicole Ippolito
(74) *Attorney, Agent, or Firm* — Womble Bond Dickinson (US) LLP; Deborah M. Vernon; Heath T. Misley

(57) ABSTRACT

An analytical instrument is disclosed comprising a liquid chromatography system comprising a first column, a chromatographic delay line and a splitter arranged and adapted in a mode of operation to split eluent from the first column into a first portion of eluent and a second portion of eluent. The instrument further comprises a first device. The liquid chromatography system is arranged and adapted in the mode of operation: (i) to pass the first portion of eluent from the splitter to the first device such that a first part of the first portion of eluent arrives at the first device at a first time ti and a second part of the first portion of eluent arrives at the first device at a second time $t_2$. The system is further arranged and adapted: (ii) to pass the second portion of eluent from the splitter through the chromatographic delay line to the first device such that the passage of the second portion of eluent from the splitter to the first device is delayed relative to the passage of the first portion of eluent from the splitter to the first device, and such that a first part of the second portion of eluent arrives at the first device at a third time $t_3$, where $t_1 < t_3 < t_2$. The analytical instrument is arranged and adapted to analyze the first part of the first portion of eluent in a first mode of operation and to analyze the first part of the second portion of eluent in a second mode of operation.

20 Claims, 1 Drawing Sheet

(58) Field of Classification Search
CPC ...... H01J 49/004; H01J 49/0422; H01J 49/26; H01J 49/04
USPC ................................ 250/281, 282, 283, 288
See application file for complete search history.

(56) References Cited

U.S. PATENT DOCUMENTS

| | | |
|---|---|---|
| 8,686,353 B2 | 4/2014 | Mayer |
| 8,741,149 B2 | 6/2014 | Hughes |
| 9,196,466 B2 | 11/2015 | Bateman |
| 2002/0121468 A1* | 9/2002 | Fischer .................. G01N 30/82 210/198.2 |
| 2003/0136904 A1 | 7/2003 | Mukaibatake |
| 2011/0089318 A1* | 4/2011 | Mayer ................ G01N 30/7233 250/282 |
| 2014/0014585 A1* | 1/2014 | Dourdeville ........... G01N 30/04 210/656 |

* cited by examiner

STAGGERED CHROMATOGRAPHY MASS SPECTROMETRY

CROSS-REFERENCE TO RELATED APPLICATIONS

This application represents the U.S. National Phase of International Application number PCT/GB2015/000177 entitled "Staggered Chromatography Mass Spectrometry" filed 12 Jun. 2015, which claims priority from and the benefit of United Kingdom patent application No. 1410521.7 filed on 12 Jun. 2014. The entire contents of these applications are incorporated herein by reference.

FIELD OF THE INVENTION

The present invention relates to an analytical instrument and a method of analysing a sample.

BACKGROUND

Liquid chromatography ("LC") is a method by which various species from a complex mixture can be separated out into their individual components. The individual species or components will elute from the liquid chromatography system at substantially different times.

A liquid chromatography system used in conjunction with a mass spectrometer ("MS") or a tandem mass spectrometer ("MS/MS") represents a powerful analytical instrument. However, the relatively short time that any particular analyte species is present in the ion source of the mass spectrometer limits the quality of data that can be achieved. Similarly, the length of time that any particular species of parent ion is present in the ion source limits the number of different MS/MS product ion mass spectra that can be measured. This length of time is determined by the peak elution profile for the particular liquid chromatography system being used.

Advances in the speed of mass spectrometry analysis have enabled a greater number of quality MS and MS/MS experiments to be performed during the time scale of a liquid chromatography peak. However, limitations still exist as the peak elution time can be faster than the time required to perform all of the desired MS and MS/MS experiments. These limitations often result in compromises in the quality and/or quantity of experimental data produced. Furthermore, the on-going development of faster liquid chromatography systems for increased chromatographic resolution and faster analysis has compounded these problems.

U.S. Pat. No. 7,797,988 (Schultz) discloses a method wherein the eluent eluting from an LC column is split. One portion of the eluent is sent to a mass spectrometer for analysis, while at the same time the other portion is stored in a storage tube. Once the analysis of the first portion is complete, the stored portion of eluent is sent to the mass spectrometer for analysis. In this method, each chromatographic peak is introduced into the mass spectrometer twice, thereby theoretically doubling the time available for mass spectrometry experiments.

However, using this method it can be difficult to precisely predict when a delayed chromatographic peak corresponding to a particular chromatographic peak of interest will be introduced to the mass spectrometer and it can therefore be difficult to exploit the delayed peak fully (i.e. by performing the desired additional experiments at the appropriate time). This uncertainty is mainly due to the relatively long delay times inherent in the method (which are typically very long when compared to a single chromatographic run), but additional uncertainty is also introduced by unpredictable diffusion/mixing effects that arise when the flow of the eluent is stopped.

It is also known to attempt to effectively extend the time that a peak elutes by reducing the flow rate through a liquid chromatography system when species of interest are identified by a mass spectrometer. This technique is known as peak parking or variable flow chromatography. For example, US 2006/0186028 (Micromass) discloses an arrangement wherein separate pumps are used to effect variable flow chromatography. These arrangements do not suffer from uncertainty in the delay time because a peak of interest is simply extended. However, these arrangements require accurate control of the liquid chromatography flow rate and can therefore be relatively complex. Varying the liquid chromatography flow rate can also affect the chromatographic performance and chromatographic resolution.

It is therefore desired to provide an improved analytical instrument and an improved method of analysing a sample.

SUMMARY

According to an aspect there is provided an analytical instrument comprising:

a liquid chromatography system comprising a first column, a chromatographic delay line and a splitter arranged and adapted in a mode of operation to split eluent from the first column into a first portion of eluent and a second portion of eluent; and at least one first device;

wherein the liquid chromatography system is arranged and adapted in the mode of operation: (i) to pass the first portion of eluent from the splitter to the first device such that a first part of the first portion of eluent arrives at the first device at a first time $t_1$ and a second part of the first portion of eluent arrives at the first device at a second time $t_2$; and (ii) to pass the second portion of eluent from the splitter through the chromatographic delay line to the first device such that the passage of the second portion of eluent from the splitter to the first device is delayed relative to the passage of the first portion of eluent from the splitter to the first device, and such that a first part of the second portion of eluent arrives at the first device at a third time $t_3$, where $t_1 < t_3 < t_2$;

wherein the analytical instrument is arranged and adapted:

to analyse the first part of the first portion of eluent in a first mode of operation; and to analyse the first part of the second portion of eluent in a second mode of operation.

Various embodiments relate to an analytical instrument comprising a liquid chromatography system that comprises a first chromatographic column, a splitter downstream of the column, and a chromatographic delay line arranged downstream of the splitter. A first device may be arranged downstream of the first column, the splitter and the chromatographic delay line. The first device may comprise, for example, a port or an outlet of the liquid chromatography system, or a separate device such as a combiner, an ion source or an analyser, such as a chromatography detector, a mass spectrometer or an ion mobility spectrometer. The mass spectrometer may comprise any type of mass spectrometer, such as for example, a tandem mass spectrometer, ion mobility spectrometer, and the like. In use, eluent may be passed from the column to the first device optionally via the delay line.

According to various embodiments, in a mode of operation, eluent from the column is split, and the portion of eluent that passes from the splitter to the first device via the chromatographic delay line is delayed relative to the other portion of eluent that passes from the splitter to the first device without passing through the delay line. The delay line may comprise, for example, an arrangement of tubing having a relatively extended path length, a device that restricts the speed of a fluid passing through it and/or one or more additional chromatographic columns.

In an embodiment, the system initially operates in a mode of operation in which substantially all of (or at least a portion of) the eluent from the first column is passed to an analyser (e.g. to an ion source of a mass spectrometer), in an embodiment without passing the eluent through the chromatographic delay line. Accordingly, in this mode of operation eluent from the first column may be (optionally ionised and) analysed by the analytical instrument (mass spectrometer) in a substantially conventional manner.

In an embodiment, the system may be triggered to switch to the mode of operation in which the eluent from the first column is split, and the first portion is passed to the analyser through the chromatographic delay line, while the second portion is passed substantially directly to the analyser i.e. without passing the eluent through the chromatographic delay line.

Accordingly, in this mode of operation, different portions of a particular analyte (liquid chromatography peak) eluting from the chromatographic column at a particular time will arrive at the analyser at different times. The time that the particular analyte (liquid chromatography peak) is present in the analyser can thereby be extended.

In an embodiment, the delay time between the first and second portions of eluent is relatively short, such that the first and second portions of eluent "overlap" in time, i.e. at the first device. In an embodiment, the delay time between the first and second portions of eluent is (much) less than the time taken for a single liquid chromatography run. In an embodiment, chromatographic peaks from the second portion of eluent are delayed relative to the corresponding chromatographic peaks in the first portion of eluent by a delay time (in an embodiment much less than the time taken for a single liquid chromatography run) such that the delayed peaks effectively appear before the end of the liquid chromatography run (i.e. during the elution of the non-delayed first portion of eluent).

Furthermore, the analytical instrument may be configured to switch its mode of operation such that the corresponding chromatographic peaks are analysed in different modes of operation (e.g. of the mass spectrometer), i.e. the analytical instrument (mass spectrometer) may be configured to switch its mode of operation within the time scale of a single chromatographic run.

This then advantageously means that additional information (from the different modes of operation) can be acquired about a particular chromatographic peak substantially within the time scale of a single chromatographic run.

In one embodiment, the delay time is short enough that the non-delayed peak and the delayed peak partially overlap in time, i.e. such that a chromatographic peak of interest is effectively extended in time. In another embodiment, the delay time is short enough that the non-delayed peak and the delayed peak occur next to one another in time (i.e. in an embodiment without any other peaks between them).

Accordingly, it will be appreciated that embodiments can achieve staggered chromatography in a particularly simple and convenient manner. Furthermore, advantageously it is not necessary to alter the liquid chromatography flow rate to achieve this effect. Moreover, in contrast with U.S. Pat. No. 7,797,988, various embodiments do not suffer from the problems arising from uncertainty in the delay time.

In further embodiments, by varying the delay time between the separate portions of the eluent in a controlled manner, the delayed portion can be introduced into the analyser at substantially any time as desired. For example, the delay time can be set to be sufficiently long so that the analytical instrument (or the mass spectrometer) has (just enough) time to change its mode of operation between related liquid chromatography peaks.

In this way, the analytical instrument can, substantially during the time scale of a single chromatographic run, measure the same analyte (liquid chromatography peak) in the different modes of operation even when the peak elution time is relatively short, and/or when the time taken for the analytical instrument to change its mode of operation is relatively long. Furthermore, in these embodiments it becomes possible to avoid changing the mode of operation of the analytical instrument (mass spectrometer) while an analyte (liquid chromatography peak) of interest is present in the analyser, thereby increasing the overall duty cycle of the system.

Thus, various embodiments go beyond known "peak parking" arrangements and allow greater control over the analyte thereby providing an increased duty cycle and improved quality and depth of mass spectral data.

It will therefore be appreciated that various embodiments provide a particularly advantageous analytical instrument.

The first column may comprise a High Performance Liquid Chromatography ("HPLC") column.

In an embodiment, the liquid chromatography system is arranged and adapted such that the time $\Delta t_1$ taken for the first portion of eluent to pass from the splitter to the first device is less than the time $\Delta t_2$ taken for the second portion of eluent to pass from the splitter to the first device.

In an embodiment, the delay time $\Delta T = \Delta t_2 - \Delta t_1$ is fixed or variable.

In an embodiment, the delay time $\Delta T$ is selected from the group consisting of: (i) <1 s; (ii) 1-2 s; (iii) 2-5 s; (iv) 5-10 s; (v) 10-15 s; (vi) 15-20 s; (vii) 20-30 s; (viii) 30-40 s; (ix) 40-50 s; (x) 50-60 s; (xi) >60 s.

In an embodiment:
the first part of the first portion of eluent comprises eluent eluted from the first column at a first retention time;
the second part of the first portion of eluent comprises eluent eluted from the first column at a second retention time; and
the first part of the second portion of eluent comprises eluent eluted from the first column at a third retention time.

In an embodiment, the first part of the first portion of eluent and the first part of the second portion of eluent comprise eluent eluted from the first column at the same retention time.

In an embodiment:
the first part of the first portion of eluent comprises a first chromatographic peak of the first portion of eluent;
the second part of the first portion of eluent comprises a second chromatographic peak of the first portion of eluent; and
the first part of the second portion of eluent comprises a third chromatographic peak of the second portion of eluent.

In an embodiment, the first chromatographic peak and the third chromatographic peak are corresponding chromatographic peaks from the same chromatographic peak of the eluent.

In an embodiment, the analytical instrument is arranged and adapted to select the third time $t_3$ such that the part of the first portion of eluent that arrives at the first device at the third time $t_3$ comprises no chromatographic peaks or comprises relatively unimportant, uninteresting and/or low intensity chromatographic peaks.

In an embodiment, the chromatographic delay line comprises an arrangement of tubing.

In an embodiment, the chromatographic delay line comprises one or more second columns.

The one or more second columns may comprise one or more High Performance Liquid Chromatography ("HPLC") columns.

In an embodiment, the system is arranged and adapted such that the path length $\Delta d_1$ for the first portion of eluent to pass from the splitter to the first device is shorter than the path length $\Delta d_2$ for the second portion of eluent to pass from the splitter to the first device.

In an embodiment, the path difference $\Delta D = \Delta d_2 - \Delta d_1$ is fixed or variable.

In an embodiment, the system is arranged and adapted such that the average speed or velocity $\Delta v_1$ of the first portion of eluent as it passes from the splitter to the first device is greater than the average speed or velocity $\Delta v_2$ of the second portion of eluent as it passes from the splitter to the first device.

In an embodiment, the difference in the average speed or velocity $\Delta V = \Delta v_2 - \Delta v_1$ is fixed or variable.

In an embodiment, the first device is arranged and adapted to combine the first and second portions of eluent.

In an embodiment, the system is arranged and adapted such that the eluent flows continuously as it passes from the first column to the first device.

In an embodiment, the system is arranged and adapted such that:

the first portion of eluent flows continuously as it passes from the first column to the first device; and the second portion of eluent flows continuously as it passes from the first column through the chromatographic delay line to the first device. This advantageously avoids (or minimises) problems with component diffusion that arise when the flow of an eluent is stopped.

In an embodiment, the system is arranged and adapted in a further mode of operation to pass substantially all eluent from the first column to the first device without passing the eluent through the chromatographic delay line.

In an embodiment, the system is arranged and adapted such that in the further mode of operation the splitter is bypassed or is configured so as not to split eluent from the first column such that substantially all eluent from the first column passes to the first device without passing through the chromatographic delay line.

In an embodiment, the system is arranged and adapted to switch from the further mode of operation to the splitting mode of operation upon the instrument determining, analysing, measuring, detecting, predicting or estimating that one or more analytes, components or chromatographic peaks of interest are emerging, eluting or being transmitted from the first column.

In an embodiment, the system is arranged and adapted to switch from the splitting mode of operation to the further mode of operation after a predetermined time.

The predetermined time may be selected from the group consisting of: (i) <1 s; (ii) 1-10 s; (iii) 10-20 s; (iv) 20-30 s; (v) 30-40 s; (vi) 40-50 s; (vii) 50-60 s; (viii) 60-70 s; (ix) 70-80 s; (x) 80-90 s; (xi) 90-100 s; (xii) 100-110 s; (xiii) 110-120 s; (xiv) 120-130 s; (xv) 130-140 s; (xvi) 140-150 s; (xvii) 150-160 s; (xviii) 160-170 s; (xix) 170-180 s; (xx) 180-190 s; (xxi) 190-200 s; (xxii) 200-210 s; (xxiii) 210-220 s; (xxiv) 220-230 s; (xxv) 230-240 s; (xxvi) 240-250 s; (xxvii) 250-260 s; (xxviii) 260-270 s; (xxix) 270-280 s; (xxx) 280-290 s; (xxxi) 290-300 s; and (xxxii) >300 s.

In an embodiment:

the system is arranged and adapted to switch from the further mode of operation to the splitting mode of operation during a single experimental run or acquisition; and/or the system is arranged and adapted to switch from the splitting mode of operation to the further mode of operation during the single experimental run or acquisition.

In an embodiment, the system is arranged and adapted in the splitting mode of operation to pass the first portion of eluent from the splitter to the first device and to pass the second portion of eluent from the splitter to the first device at the same time.

In an embodiment, the liquid chromatography system further comprises:

one or more second chromatographic delay lines;

wherein the system is arranged and adapted in a mode of operation to split the eluent into one or more third portions of eluent and to pass the one or more third portions of eluent from the splitter through the one or more second chromatographic delay lines to the first device.

The system may further comprise a fluid delivery system for delivering a fluid to the first column.

The fluid delivery system may comprise an aqueous solvent or solution delivery device arranged and adapted to dispense an aqueous solvent or solution.

The fluid delivery system may comprise an organic solvent delivery device arranged and adapted to dispense an organic solvent.

The organic solvent may be selected from the group consisting of: (i) acetonitrile; (ii) methanol; (iii) propanol; (iv) an alcohol; and (v) tetrahydrofuran ("THF").

The fluid delivery system may comprise an analyte delivery device arranged and adapted to dispense an analyte.

The fluid delivery system may be arranged and adapted to mix the flows from the aqueous solvent or solution delivery device, the organic solvent delivery device and the analyte delivery device so as to provide an isocratic flow of fluid to the first column.

The fluid delivery system may be arranged and adapted to pass fluid through the first column at a flow rate selected from the group consisting of: (i) <10 nl/min; (ii) 10-20 nl/min; (iii) 20-30 nl/min; (iv) 30-40 nl/min; (v) 40-50 nl/min; (vi) 50-60 nl/min; (vii) 60-70 nl/min; (viii) 70-80 nl/min; (ix) 80-90 nl/min; (x) 90-100 nl/min; (xi) 100-200 nl/min; (xii) 200-300 nl/min; (xiii) 300-400 nl/min; (xiv) 400-500 nl/min; (xv) 500-600 nl/min; (xvi) 600-700 nl/min; (xvii) 700-800 nl/min; (xviii) 800-900 nl/min; (xix) 900-1000 nl/min; (xx) 1-100 μl/min; (xxi) 100-200 μl/min; (xxii) 200-300 μl/min; (xxiii) 300-400 μl/min; (xxiv) 400-500 μl/min; (xxv) 500-600 μl/min; (xxvi) 600-700 μl/min; (xxvii) 700-800 μl/min; (xxviii) 800-900 μl/min; (xxix) 900-1000 μl/min; (xxx) 1.0-2.0 ml/min; (xxxi) 2.0-3.0 ml/min; (xxxii) 3.0-4.0 ml/min; (xxxiii) 4.0-5.0 ml/min; (xxxiv) 5.0-6.0 ml/min; (xxxv) 6.0-7.0 ml/min; (xxxvi) 7.0-8.0 ml/min; (xxxvii) 8.0-9.0 ml/min; (xxxviii) 9.0-10.0 ml/min; and (xxxix) >10.0 ml/min.

The fluid delivery system may be arranged and adapted to maintain a substantially continuous flow of fluid through the first column.

The fluid delivery system may be arranged and adapted to maintain a substantially constant or regular flow of fluid through the first column.

Alternatively or additionally, the fluid delivery system may be arranged and adapted to alter or vary the flow rate at which fluid is passed through the first column.

In an embodiment, the system is arranged and adapted to alter or vary the flow rate at which fluid is passed through the first column upon the instrument determining, analysing, measuring, detecting, predicting or estimating that one or more analytes, components or chromatographic peaks of interest are emerging, eluting or being transmitted from the first column.

In an embodiment, the first device comprises a port or an outlet of the liquid chromatography system.

In an embodiment, the first device comprises a separate device arranged downstream of the liquid chromatography system.

In an embodiment, the first device comprises an analyser.

In an embodiment, the instrument further comprises an analyser downstream of the first device.

In an embodiment, the analyser is arranged and adapted:
to analyse the first part of the first portion of eluent in the first mode of operation; and
to analyse the first part of the second portion of eluent in the second mode of operation.

In an embodiment, the analyser comprises a chromatography detector.

In an embodiment, the chromatography detector comprises:
a destructive chromatography detector in an embodiment selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or
a non-destructive chromatography detector in an embodiment selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

In an embodiment, the analyser comprises an ion detector such as a mass spectrometer or an ion mobility spectrometer.

In an embodiment, the first device comprises an ion source or the instrument further comprises an ion source. In an embodiment, the ion source is part of the analyser. The analytical instrument may comprise an ion source coupled to the first column. In embodiment, the first device is an ion source.

The ion source may be selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source;

The ion source may comprise a continuous ion source.

Alternatively, the ion source may comprise a pulsed ion source.

In an embodiment, the liquid chromatography system is arranged and adapted to switch from the further mode of operation to the splitting mode of operation upon the instrument determining, analysing, measuring, detecting, predicting or estimating that one or more analytes, components or chromatographic peaks of interest are being eluted to the ion source and/or that ions of interest are being emitted from the ion source.

In an embodiment, the instrument is arranged and adapted:
to analyse ions derived from the first part of the first portion of eluent in the first mode of operation; and
to analyse ions derived from the first part of the second portion of eluent in the second mode of operation.

In an embodiment, the instrument further comprises an ion detector. The ion detector may be part of the analyser, e.g. the mass spectrometer or ion mobility spectrometer.

In an embodiment, the ion detector comprises a mass analyser which may be selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

In an embodiment, the liquid chromatography system is arranged and adapted to switch from the further mode of operation to the splitting mode of operation upon the ion detector detecting ions of interest.

In an embodiment, the first and/or second mode of operation comprises:
a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation; a Quantification mode of operation; or an Ion Mobility Spectrometry ("IMS") mode of operation.

The first and/or second mode of operation may comprise:
(i) a Collisional Induced Dissociation ("CID") mode of operation; (ii) a Surface Induced Dissociation ("SID") mode of operation; (iii) an Electron Transfer Dissociation ("ETD") mode of operation; (iv) an Electron Capture Dissociation ("ECD") mode of operation; (v) an Electron Collision or Impact Dissociation mode of operation; (vi) a Photo Induced Dissociation ("PID") mode of operation; (vii) a Laser Induced Dissociation mode of operation; (viii) an infrared radiation induced dissociation mode of operation; (ix) an ultraviolet radiation induced dissociation mode of operation; (x) a nozzle-skimmer interface fragmentation mode of operation; (xi) an in-source fragmentation mode of operation; (xii) an in-source Collision Induced Dissociation mode of operation; (xiii) a thermal fragmentation mode of operation; (xiv) an electric field induced fragmentation mode of operation; (xv) a magnetic field induced fragmentation mode of operation; (xvi) an enzyme digestion or enzyme degradation fragmentation mode of operation; (xvii) an ion-ion reaction fragmentation mode of operation; (xviii) an ion-molecule reaction fragmentation mode of operation; (xix) an ion-atom reaction fragmentation mode of operation; (xx) an ion-metastable ion reaction fragmentation mode of operation; (xxi) an ion-metastable molecule reaction fragmentation mode of operation; (xxii) an ion-metastable atom reaction fragmentation mode of operation; (xxiii) an ion-ion reaction mode of operation wherein ions react to form adduct or product ions; (xxiv) an ion-molecule reaction mode of operation wherein ions react to form adduct or product ions; (xxv) an ion-atom reaction mode of operation wherein ions react to form adduct or product ions; (xxvi) an ion-metastable ion reaction mode of operation wherein ions react to form adduct or product ions; (xxvii) an ion-metastable molecule reaction mode of operation wherein ions react to form adduct or product ions; (xxviii) an ion-metastable atom reaction mode of operation wherein ions react to form adduct or product ions; or (xxix) an Electron Ionisation Dissociation ("EID") mode of operation.

In an embodiment, the second mode of operation comprises an optimised version of the first mode of operation.

In an embodiment, the analytical instrument is arranged and adapted to select and/or optimise the second mode of operation based on information acquired from the first portion of eluent analysed in the first mode of operation.

In an embodiment, the analytical instrument is arranged and adapted:

to analyse the second part of the first portion of eluent in the first and/or second and/or another mode of operation.

In an embodiment, the first portion of eluent comprises x % of the eluent from the first column, and the second portion of eluent comprises y % of the eluent from the second column, wherein the ratio x:y is selected from the group consisting of: (i) 1:9 to 1:4; (ii) 1:4 to 3:7; (iii) 3:7 to 2:3; (iv) 2:3 to 1:1; (v) 1:1 to 3:2; (vi) 3:2 to 7:3; (vii) 7:3 to 4:1; (viii) 4:1 to 9:1.

In an embodiment, the analytical instrument further comprises a liquid phase labelling or modification device arranged and adapted to label or modify the first and/or second part of the first and/or second portion of the eluent.

In an embodiment, the liquid phase labelling or modification device is selected from the group consisting of: (i) a hydrogen deuterium exchange device; (ii) a supercharging device; (iii) a charge stripping device; (iv) a fluorescence device; (v) a fast photochemical oxidation of protein ("FPOP") device; and (vi) a fast on-column digestion device.

In an embodiment, the at least one first device comprises two or more first devices.

In an embodiment, the liquid chromatography system is arranged and adapted in the mode of operation: (i) to pass the first portion of eluent from the splitter to one of the first devices such that a first part of the first portion of eluent arrives at the one first device at a first time $t_1$ and a second part of the first portion of eluent arrives at the one first device at a second time $t_2$; and (ii) to pass the second portion of eluent from the splitter through the chromatographic delay line to another of the first devices such that the passage of the second portion of eluent from the splitter to the another first device is delayed relative to the passage of the first portion of eluent from the splitter to the one first device, and such that a first part of the second portion of eluent arrives at the another first device at a third time $t_3$, where $t_1 < t_3 < t_2$.

In an embodiment, the first column has an internal diameter selected from the group consisting of: (i) <50 µm; (ii) 50-100 µm; (iii) 100-200 µm; (iv) 200-300 µm; (v) 300-400 µm; (vi) 400-500 µm; (vii) 500-600 µm; (viii) 600-700 µm; (ix) 700-800 µm; (x) 800-900 µm; (xi) 900-1000 µm; (xii) 1.0-1.5 mm; (xiii) 1.5-2.0 mm; (xiv) 2.0-2.5 mm; (xv) 2.5-3.0 mm; (xvi) 3.0-3.5 mm; (xvii) 3.5-4.0 mm; (xviii) 4.0-4.5 mm; (xix) 4.5-5.0 mm; (xx) 5.0-5.5 mm; (xxi) 5.5-6.0 mm; (xxii) 6.0-6.5 mm; (xxiii) 6.5-7.0 mm; (xxiv) 7.0-7.5 mm; (xxv) 7.5-8.0 mm; (xxvi) 8.0-8.5 mm; (xxvii) 8.5-9.0 mm; (xxviii) 9.0-9.5 mm; (xxix) 9.5-10.0 mm; and (xxx) >10.0 mm.

In an embodiment, the first column has a length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; (xxi) 200-210 mm; (xxii) 210-220 mm; (xxiii) 220-230 mm; (xxiv) 230-240 mm; (xxv) 240-250 mm; (xxvi) 250-260 mm; (xxvii) 260-270 mm; (xxviii) 270-280 mm; (xxix) 280-290 mm; (xxx) 290-300 mm; and (xxxi) >300 mm.

In an embodiment, the first column comprises C4, C8 or C18 stationary phase.

In an embodiment, the first column comprises particles having a size selected from the group consisting of: (i) <1 µm; (ii) 1-2 µm; (iii) 2-3 µm; (iv) 3-4 µm; (v) 4-5 µm; (vi) 5-6 µm; (vii) 6-7 µm; (viii) 7-8 µm; (ix) 8-9 µm; (x) 9-10 µm; (xi) 10-15 µm; (xii) 15-20 µm; (xiii) 20-25 µm; (xiv) 25-30 µm; (xv) 30-35 µm; (xvi) 35-40 µm; (xvii) 40-45 µm; (xviii) 45-50 µm; (xix) >50 µm.

In an embodiment, the first column comprises particles having a pore size selected from the group consisting of: (i) <10 nm; (ii) 10-20 nm; (iii) 20-30 nm; (iv) 30-40 nm; (v) 40-50 nm; (vi) 50-60 nm; (vii) 60-70 nm; (viii) 70-80 nm; (ix) 80-90 nm; (x) 90-100 nm; and (xi) >100 nm.

At least one of the one or more second columns may have an internal diameter selected from the group consisting of: (i) <50 µm; (ii) 50-100 µm; (iii) 100-200 µm; (iv) 200-300 µm; (v) 300-400 µm; (vi) 400-500 µm; (vii) 500-600 µm; (viii) 600-700 µm; (ix) 700-800 µm; (x) 800-900 µm; (xi) 900-1000 µm; (xii) 1.0-1.5 mm; (xiii) 1.5-2.0 mm; (xiv) 2.0-2.5 mm; (xv) 2.5-3.0 mm; (xvi) 3.0-3.5 mm; (xvii) 3.5-4.0 mm; (xviii) 4.0-4.5 mm; (xix) 4.5-5.0 mm; (xx) 5.0-5.5 mm; (xxi) 5.5-6.0 mm; (xxii) 6.0-6.5 mm; (xxiii) 6.5-7.0 mm; (xxiv) 7.0-7.5 mm; (xxv) 7.5-8.0 mm; (xxvi) 8.0-8.5 mm; (xxvii) 8.5-9.0 mm; (xxviii) 9.0-9.5 mm; (xxix) 9.5-10.0 mm; and (xxx) >10.0 mm.

At least one of the one or more second columns may have a length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; (xxi) 200-210 mm; (xxii) 210-220 mm; (xxiii) 220-230 mm; (xxiv) 230-240 mm; (xxv) 240-250 mm; (xxvi) 250-260 mm; (xxvii) 260-270 mm; (xxviii) 270-280 mm; (xxix) 280-290 mm; (xxx) 290-300 mm; and (xxxi) >300 mm.

At least one of the one or more second columns may comprise C4, C8 or C18 stationary phase.

At least one of the one or more second columns may comprise particles having a size selected from the group consisting of: (i) <1 µm; (ii) 1-2 µm; (iii) 2-3 µm; (iv) 3-4 µm; (v) 4-5 µm; (vi) 5-6 µm; (vii) 6-7 µm; (viii) 7-8 µm; (ix) 8-9 µm; (x) 9-10 µm; (xi) 10-15 µm; (xii) 15-20 µm; (xiii) 20-25 µm; (xiv) 25-30 µm; (xv) 30-35 µm; (xvi) 35-40 µm; (xvii) 40-45 µm; (xviii) 45-50 µm; (xix) >50 µm.

At least one of the one or more second columns may comprise particles having a pore size selected from the group consisting of: (i) <10 nm; (ii) 10-20 nm; (iii) 20-30 nm; (iv) 30-40 nm; (v) 40-50 nm; (vi) 50-60 nm; (vii) 60-70 nm; (viii) 70-80 nm; (ix) 80-90 nm; (x) 90-100 nm; and (xi) >100 nm.

According to an aspect there is provided a method of analysing a sample comprising:

providing a liquid chromatography system comprising a first column and a chromatographic delay line;

splitting an eluent from the first column into a first portion of eluent and a second portion of eluent;

providing at least one first device;

passing the first portion of eluent from the splitter to the first device such that a first part of the first portion of eluent arrives at the first device at a first time $t_1$ and a second part of the first portion of eluent arrives at the first device at a second time $t_2$;

passing the second portion of eluent from the splitter through the chromatographic delay line to the first device, such that the passage of the second portion of eluent from the splitter to the first device is delayed relative to the passage of the first portion of eluent from the splitter to the first device, and such that a first part of the second portion of eluent arrives at the first device at a third time $t_3$, where $t_1 < t_3 < t_2$;

analysing the first part of the first portion of eluent in a first mode of operation; and analysing the first part of the second portion of eluent in a second mode of operation.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Figure 1:
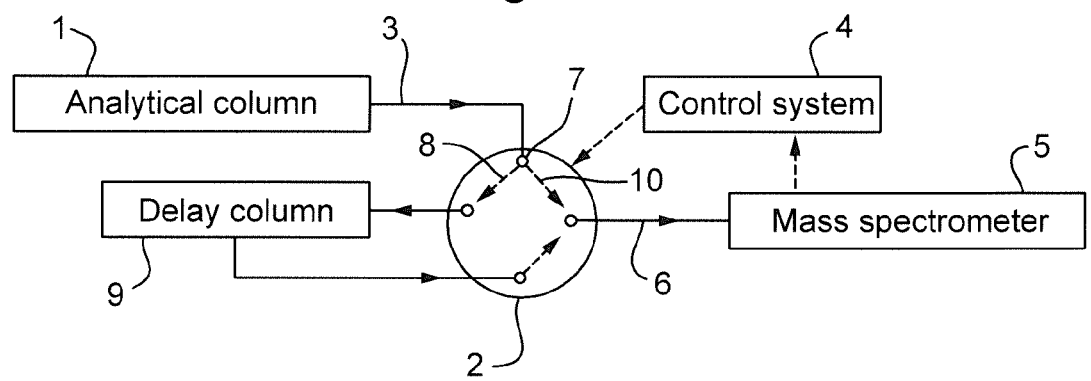
FIG. 1 schematically shows a liquid chromatography system in accordance with an embodiment.

An embodiment will now be described. FIG. 1 shows an embodiment wherein eluent from an analytical column 1 is coupled to a switching valve 2 via tubing 3. A control system 4 may be used to control the switching valve 2.

In a ("splitting") mode of operation the eluent is split by splitting valve 7 so that a portion of the eluent passes to the mass spectrometer 5 via a connection 8, via a delay column 9 and tubing 6 while (at the same time) another portion of the eluent passes to the mass spectrometer 5 via connection 10 and tubing 6. The two portions of the eluent may comprise corresponding portions of eluent (i.e. the splitting valve may continuously split the eluent into corresponding first and second portions over a period of time) and therefore in an embodiment corresponding chromatographic peaks.

It will be understood that as used herein, the first and second "portions" of eluent may comprise eluent from an entire chromatographic run e.g. in an embodiment they may comprise chromatographic peaks from an entire chromatographic run. The "parts" of the portions of eluent may be eluent from less than the entire chromatographic run such as, for example, eluent comprising a single chromatographic peak.

In another mode of operation the eluent is not split and passes direct to the mass spectrometer 5 via tubing 6.

The chromatographic splitting valve 7 may be used to divert a portion of the liquid chromatography eluent into a delaying column or chromatographic delay line 9 for subsequent analysis under different mass spectrometer analysis modes or conditions. The chromatographic eluent is selectively split during the liquid chromatography run into the delaying column 9. The delay time introduced by the column 9 may allow the mass spectrometer system 5 time to be adjusted and optimised for a new set of extended experiments when the delayed peak(s) are allowed through at a later time in the same run.

The two portions of the eluent that are split may be re-combined before being analysed. Accordingly, the two portions may be analysed by the mass spectrometer 5 together, at the same time. In an embodiment, the eluent flows through the analytical column 1 and to the mass spectrometer 5 in a substantially continuous manner i.e. without being stopped at any point. This advantageously avoids problems that can occur with stationary eluent such as mixing/diffusion of analytes etc.

The delay time between the first and second portions of eluent may be selected such that the first and second portions of eluent "overlap" in time i.e. at the mass spectrometer 5. In an embodiment, the delay time between the first and second portions of eluent may be (much) less than the time taken for a single liquid chromatography run. In an embodiment, chromatographic peaks from the second portion of eluent may be delayed relative to the corresponding chromatographic peaks in the first portion of eluent by a delay time (in an embodiment much less than the time taken for a single liquid chromatography run) such that the delayed peaks effectively appear before the end of the liquid chromatography run (i.e. during the elution of the non-delayed first portion of eluent).

The mass spectrometer may be configured to switch its mode of operation such that the corresponding chromatographic peaks are analysed in different modes of operation, i.e. the mass spectrometer may be configured to switch its mode of operation within the time scale of a single chromatographic run.

This then means that additional information (from the different modes of operation) can be acquired about a particular chromatographic peak, advantageously within the time scale of a single chromatographic run, e.g. without significantly extending the time taken for the experiment.

Relatively short delay times according to various embodiments are also advantageous because they reduce and/or avoid any adverse effects on the delayed portion of eluent, e.g. due to diffusion of analytes, etc. Furthermore, shorter delay times facilitate accurate prediction of when a particular analyte (chromatographic peak) will (re-) appear in the ion source (i.e. when compared with longer delay times), which means that the timing of the switching of the mass spectrometer 5 can be optimised, e.g. to maximise the duty cycle of the system.

The eluent may be split into the two portions using any ratio as desired, such as for example, 1:1, 1:2 or 2:1. In embodiments where the ratio of the splitting is not 1:1, the second, delayed portion may be larger than the first, non-delayed portion. In an alternative embodiment, the second, delayed portion may be smaller than the first, non-delayed portion. In one embodiment where the ratio of the splitting is not 1:1, a measurement of the relative intensity of a chromatographic peak and/or of ions derived from a chromatographic peak (i.e. the intensity of a measurement by an analyser such as a chromatography detector, mass spectrometer or ion mobility spectrometer) may be used to aid in identifying the chromatographic peak (or ions), i.e. to aid in identifying whether the peak (or ions) is from the delayed portion of eluent or from the non-delayed portion of eluent. Relatively intense chromatographic peaks (or ions) will tend to be from the larger portion of eluent, and vice versa.

The mass spectrometer 5 can be switched between any desired modes of operation, so as to analyse corresponding chromatographic peaks in different modes of operation. For example, the mass spectrometer can be switched between mass spectrometry ("MS") modes of operation, tandem mass spectrometry ("MS/MS") modes of operation, $MS^E$ modes of operation (in which parent ions are alternatively fragmented or reacted, and not fragmented or reacted or fragmented or reacted to a lesser degree), Multiple Reaction Monitoring ("MRM") modes of operation, Data Dependent Analysis ("DDA") modes of operation, Data Independent Analysis ("DIA") modes of operation, Quantification modes of operation, and/or Ion Mobility Spectrometry ("IMS") modes of operation.

The mass spectrometer 5 may be switched between various fragmentation modes of operation, so as to fragment or react parent ions from the corresponding chromatographic peaks in different modes.

In an embodiment, the second mode of operation is an optimised version of the first mode of operation. In an embodiment, the second mode of operation corresponds to the first mode of operation, but with different conditions. Any of the parameters of the analytical instrument may be optimised or changed between the modes of operation, such as for example, values or ranges of mass, mass to charge ratio, ion mobility, fragmentation or collision energy, voltages, gases, etc.

The second mode of operation may be selected and/or optimised based on data acquired relating to the first portion of eluent.

In an example embodiment, the cone voltage of an nozzle-skimmer interface may initially be optimised for transmission of 2+ ions for subsequent fragmentation in a Collision Induced Dissociation ("CID") fragmentation device for the primary (initial) liquid chromatography peak. For a delayed peak, the cone voltage may then be reduced and optimised for transmission of 3+ or 4+ ions so that Electron Transfer Dissociation ("ETD") can be performed in an Electron Transfer Dissociation fragmentation device.

In another example embodiment, the mass spectrometer may be switched between an IMS mode of operation and a fragmentation, collision or reaction mode of operation, such as an ETD mode of operation, e.g. by altering the gas present within an ion guide of the mass spectrometer 5.

In another example embodiment, the presence of an ion of interest can cause the mass spectrometer to switch from an $MS^E$ or "Shotgun" mode of operation to an MRM mode of operation.

In another example embodiment, if a first (non-delayed) chromatographic peak (or ions present within the first chromatographic peak) saturates the detector of the mass spectrometer 5, the gain of the detector can be reduced when measuring the corresponding delayed chromatographic peak, e.g. so as to improve quantification. Alternatively, the gain can be increased when measuring the corresponding delayed peak, e.g. so as to better analyse lower intensity ions. In another embodiment, instead of increasing or decreasing the gain of the mass spectrometer 5 detector, a diluting solvent can be added to (or subtracted from) the delayed portion of eluent, so as to drop the concentration of the delayed eluent.

In an embodiment, the delay time $\Delta T$ can be fixed. In this embodiment, known deconvolution techniques may be used (if necessary) to separate delayed mass spectrometry data from non-delayed data.

In one embodiment, a first non-delayed chromatographic peak is analysed by the instrument in a first mode of operation, and a corresponding first delayed chromatographic peak is analysed by the instrument in a second, different mode of operation. If a second non-delayed chromatographic peak happens to be present at the same time as the first delayed chromatographic peak, then the instrument may be configured to switch its mode of operation again, e.g. so as to analyse the second chromatographic peak the first mode of operation or in a third different mode of operation.

In an embodiment, the delay time $\Delta T$ can be adjusted so that the arrival of the delayed peak(s) coincides with a region of chromatography that is less congested or is of less interest. In an embodiment, this may be targeted based on knowledge of prior liquid chromatography runs.

In an embodiment, the delay line can be switched into operation based on mass spectral information and pre-programmed criteria, e.g. associated with the primary (non-delayed) eluting peak of interest. For example, if an ion of interest is detected, the delay line can be switched into operation. Thus, it will be appreciated that embodiments provide extra time for data directed processing algorithms to target fast eluting peaks.

Figure 2A:
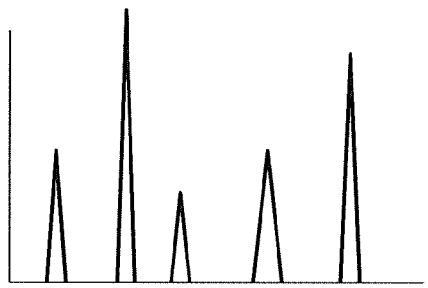
FIG. 2A shows a theoretical ion chromatogram resulting from a normal (second) mode of operation.

FIG. 2A shows a theoretical ion chromatogram resulting from a substantially conventional mode of operation. The ion chromatogram shows a number of liquid chromatography peaks as a result of different analytes being separated out by the liquid chromatography column 1.

Figure 2B:
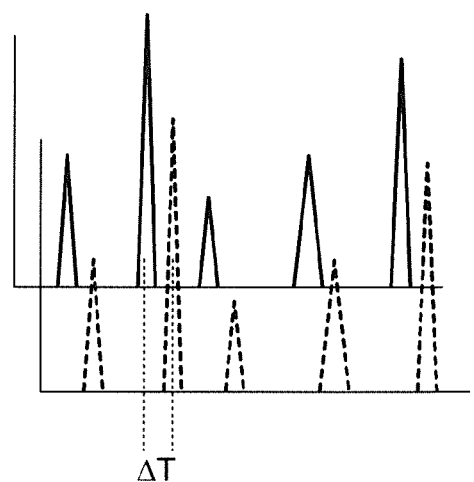
FIG. 2B shows the ion chromatogram of FIG. 2A overlaid with an identical ion chromatogram which is delayed by an amount ΔT and FIG. 2C shows the total ion chromatogram resulting from the first mode of operation.
Figure 2C:
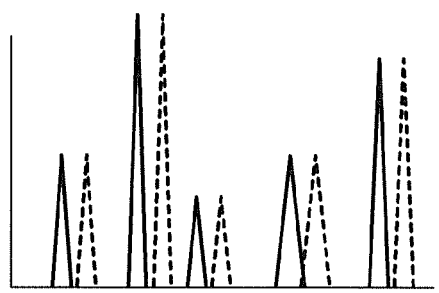

FIGS. 2B and 2C illustrate a mode of operation according to an embodiment. In this mode of operation, the eluent may be split into separate portions and the separate portions may be introduced into the mass spectrometer at different times with a delay time of $\Delta T$.

FIG. 2B shows the ion chromatogram of FIG. 2A overlaid with an identical ion chromatogram which is delayed by $\Delta T$.

FIG. 2C shows the total ion chromatogram resulting from this mode of operation.

According to an embodiment, the liquid chromatography peak may be slowed down to allow more optimised top-down Electron Transfer Dissociation ("ETD") to be performed.

In another embodiment a very intense liquid chromatography peak may be diverted and smoothed out to avoid detector saturation.

According to another embodiment in the normal (non-splitting) mode of operation, the system may pass substantially all of (or at least a portion of) the eluent from the first column through the chromatographic delay line 9 to the mass spectrometer (or other analytical instrument).

According to various embodiments, the mass spectrometer 5 in FIG. 1 may be replaced with any other type of analyser, such as for example, an ion mobility spectrometer or a chromatography detector.

The chromatography detector may comprise a destructive chromatography detector such as a Flame Ionization Detector (FID), an aerosol-based detector or Nano Quantity Analyte Detector (NQAD), a Flame Photometric Detector (FPD), an Atomic-Emission Detector (AED), a Nitrogen Phosphorus Detector (NPD), or an Evaporative Light Scattering Detector (ELSD), or a non-destructive chromatography detector such as a fixed or variable wavelength UV detector, a Thermal Conductivity Detector (TCD), a fluorescence detector, an Electron Capture Detector (ECD), a conductivity monitor, a Photoionization Detector (PID), a Refractive Index Detector (RID), a radio flow detector, or a chiral detector.

In one embodiment, a non-destructive chromatography detector may be used in conjunction with another downstream analyser, such as for example a mass spectrometer or ion mobility spectrometer. In this embodiment, information gained from the non-destructive chromatography detector may be used to control the operation of the downstream analyser. The non-destructive chromatography analyser may be used to determine more precisely when a delayed chromatographic peak (or ions derived therefrom) will be present in the downstream analyser. Accordingly, in one embodiment, the time at which the analyser switches its modes of operation may be controlled using this information.

A non-destructive detector and/or a destructive detector may be used to analyse either the delayed and/or non-delayed portion of eluent, and information gained from the analysis may be used to control the analytical instrument.

In one embodiment, one or more parts of the split eluent may be subjected to liquid phase labelling. For example, the split portion of the eluent may be caused to pass through a hydrogen deuterium exchange region, such as a liquid medium with a hydrogen deuterium exchange region, e.g. causing ions to be labelled. According to an embodiment, this labelling may be used to control the analytical instrument (e.g. mass spectrometer). In one embodiment, the analytical instrument (e.g. mass spectrometer) may be controlled to operate in a manner more appropriate to the analysis of analytes that follow in the other un-labelled portion of eluent.

Other liquid phase modifications that could be used in these embodiments include supercharging, e.g. by MNBA reagent; charge stripping, e.g. using super-bases; fluorescent labelling, e.g. of glycans; fast photochemical oxidation of proteins ("FPOP"); and/or fast on-column digestion, e.g. using urea.

In one embodiment, a fluorescence (FLR) chromatography detector in conjunction with fluorescently labelled analytes may be used in the delayed or non-delayed portion of the LC eluent, e.g. to detect very low levels of analytes of interest and to provide a signal to the instrument (e.g. mass analyser) so that the instrument can be switched into a mode appropriate for the analysis, e.g. of glycopeptides.

Although the above embodiments have been described primarily with reference to sending both the delayed and non-delayed portions of eluent to a single analytical instrument (e.g. mass spectrometer), according to another embodiment the delayed and non-delayed portions of eluent may be sent to different (e.g. separate) analytical instruments. For example, the first portion of eluent may be passed to a first instrument (e.g. analyser) and the second portion of eluent may be passed to a separate instrument (e.g. analyser). The first and second instruments may be the same type of instrument, e.g. operating in different modes of operation, or different types of instrument. According to an embodiment, the first and second instruments are arranged and adapted to communicate with one another and/or with a control system, e.g. so as to control their mutual operation.

Although the present invention has been described with reference to preferred embodiments, it will be understood by those skilled in the art that various changes in form and detail may be made without departing from the scope of the invention as set forth in the accompanying claims.

The invention claimed is:

1. An analytical instrument comprising:
   a liquid chromatography system comprising a first column, a chromatographic delay line and a splitter arranged and adapted in a mode of operation to split eluent from said first column into a first portion of eluent and a second portion of eluent; and
   at least one first device;
   wherein said liquid chromatography system is arranged and adapted in said mode of operation: (i) to pass said first portion of eluent from said splitter to said first device such that a first part of said first portion of eluent arrives at said first device at a first time $t_1$ and a second part of said first portion of eluent arrives at said first device at a second time $t_2$; and (ii) to pass said second portion of eluent from said splitter through said chromatographic delay line to said first device, such that the passage of said second portion of eluent from said splitter to said first device is delayed relative to the passage of said first portion of eluent from said splitter to said first device, and such that a first part of said second portion of eluent arrives at said first device at a third time $t_3$, where $t_1 < t_3 < t_2$;
   wherein said analytical instrument is arranged and adapted:
   to analyse said first part of said first portion of eluent in a first mode of operation; and
   to analyse said first part of said second portion of eluent in a second mode of operation.

2. An analytical instrument as claimed in claim 1, wherein said system is arranged and adapted such that the time $\Delta t_1$ taken for said first portion of eluent to pass from said splitter to said first device is less than the time $\Delta t_2$ taken for said second portion of eluent to pass from said splitter to said first device.

3. An analytical instrument as claimed in claim 2, wherein the delay time $\Delta T = \Delta t_2 - \Delta t_1$ is fixed or variable.

4. An analytical instrument as claimed in claim 1, wherein said first part of said first portion of eluent and said first part of said second portion of eluent comprise eluent eluted from said first column at the same retention time.

5. An analytical instrument as claimed in claim 1, wherein:
   said first part of said first portion of eluent comprises a first chromatographic peak of said first portion of eluent;
   said second part of said first portion of eluent comprises a second chromatographic peak of said first portion of eluent;
   said first part of said second portion of eluent comprises a third chromatographic peak of said second portion of eluent; and
   said first chromatographic peak and said third chromatographic peak are corresponding chromatographic peaks from the same chromatographic peak of said eluent.

6. An analytical instrument as claimed in claim 5, wherein said analytical instrument is arranged and adapted to select said third time $t_3$ such that the part of said first portion of eluent that arrives at said first device at said third time $t_3$ comprises no chromatographic peaks or comprises relatively unimportant, uninteresting and/or low intensity chromatographic peaks.

7. An analytical instrument as claimed in claim 1, wherein:
   said system is arranged and adapted such that the path length $\Delta d_1$ for said first portion of eluent to pass from said splitter to said first device is shorter than the path length $\Delta d_2$ for said second portion of eluent to pass from said splitter to said first device; and/or
   said system is arranged and adapted such that the average speed or velocity $\Delta v_1$ of said first portion of eluent as it passes from said splitter to said first device is greater than the average speed or velocity $\Delta v_2$ of said second portion of eluent as it passes from said splitter to said first device.

8. An analytical instrument as claimed in claim 1, wherein said system is arranged and adapted such that said eluent flows continuously as it passes from said first column to said first device.

9. An analytical instrument as claimed in claim 1, wherein said system is arranged and adapted in a further mode of operation to pass substantially all eluent from said first column to said first device without passing said eluent through said chromatographic delay line.

10. An analytical instrument as claimed in claim 9, wherein said system is arranged and adapted to switch from said further mode of operation to said splitting mode of operation upon said instrument determining, analysing, measuring, detecting, predicting or estimating that one or more analytes, components or chromatographic peaks of interest are emerging, eluting or being transmitted from said first column.

11. An analytical instrument as claimed in claim 9, wherein said first device comprises an ion source or wherein said instrument further comprises an ion source; and
wherein said liquid chromatography system is arranged and adapted to switch from said further mode of operation to said splitting mode of operation upon said instrument determining, analysing, measuring, detecting, predicting or estimating that one or more analytes, components or chromatographic peaks of interest are being eluted to said ion source and/or that ions of interest are being emitted from said ion source.

12. An analytical instrument as claimed in claim 9, further comprising an ion detector;
wherein said liquid chromatography system is arranged and adapted to switch from said further mode of operation to said splitting mode of operation upon said ion detector detecting ions of interest.

13. An analytical instrument as claimed in claim 1, wherein:
said liquid chromatography system further comprises a fluid delivery system for delivering a fluid to said first column; and
wherein said system is arranged and adapted to alter or vary the flow rate at which fluid is passed through said first column upon said instrument determining, analysing, measuring, detecting, predicting or estimating that one or more analytes, components or chromatographic peaks of interest are emerging, eluting or being transmitted from said first column.

14. An analytical instrument as claimed in claim 1, further comprising an analyser downstream of said first device, wherein said analyser is arranged and adapted:
to analyse said first part of said first portion of eluent in said first mode of operation; and
to analyse said first part of said second portion of eluent in said second mode of operation.

15. An analytical instrument as claimed in claim 14, wherein said analyser comprises a chromatography detector, a mass spectrometer or an ion mobility spectrometer.

16. An analytical instrument as claimed in claim 1, wherein said first and/or second mode of operation comprises:
a mass spectrometry ("MS") mode of operation; a tandem mass spectrometry ("MS/MS") mode of operation; a mode of operation in which parent or precursor ions are alternatively fragmented or reacted to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation; a Quantification mode of operation; or an Ion Mobility Spectrometry ("IMS") mode of operation; and/or
(i) a Collisional Induced Dissociation ("CID") mode of operation; (ii) a Surface Induced Dissociation ("SID") mode of operation; (iii) an Electron Transfer Dissociation ("ETD") mode of operation; (iv) an Electron Capture Dissociation ("ECD") mode of operation; (v) an Electron Collision or Impact Dissociation mode of operation; (vi) a Photo Induced Dissociation ("PID") mode of operation; (vii) a Laser Induced Dissociation mode of operation; (viii) an infrared radiation induced dissociation mode of operation; (ix) an ultraviolet radiation induced dissociation mode of operation; (x) a nozzle-skimmer interface fragmentation mode of operation; (xi) an in-source fragmentation mode of operation; (xii) an in-source Collision Induced Dissociation mode of operation; (xiii) a thermal fragmentation mode of operation; (xiv) an electric field induced fragmentation mode of operation; (xv) a magnetic field induced fragmentation mode of operation; (xvi) an enzyme digestion or enzyme degradation fragmentation mode of operation; (xvii) an ion-ion reaction fragmentation mode of operation; (xviii) an ion-molecule reaction fragmentation mode of operation; (xix) an ion-atom reaction fragmentation mode of operation; (xx) an ion-metastable ion reaction fragmentation mode of operation; (xxi) an ion-metastable molecule reaction fragmentation mode of operation; (xxii) an ion-metastable atom reaction fragmentation mode of operation; (xxiii) an ion-ion reaction mode of operation wherein ions react to form adduct or product ions; (xxiv) an ion-molecule reaction mode of operation wherein ions react to form adduct or product ions; (xxv) an ion-atom reaction mode of operation wherein ions react to form adduct or product ions; (xxvi) an ion-metastable ion reaction mode of operation wherein ions react to form adduct or product ions; (xxvii) an ion-metastable molecule reaction mode of operation wherein ions react to form adduct or product ions; (xxviii) an ion-metastable atom reaction mode of operation wherein ions react to form adduct or product ions; or (xxix) an Electron Ionisation Dissociation ("EID") mode of operation.

17. An analytical instrument as claimed in claim 1, wherein said second mode of operation comprises an optimised version of said first mode of operation.

18. An analytical instrument as claimed in claim 1, wherein said analytical instrument is arranged and adapted to select and/or optimise said second mode of operation based on information acquired from said first portion of eluent analysed in said first mode of operation.

19. An analytical instrument as claimed in claim 1, wherein said analytical instrument is arranged and adapted:
to analyse said second part of said first portion of eluent in said first and/or second and/or another mode of operation.

20. A method of analysing a sample comprising:
providing a liquid chromatography system comprising a first column and a chromatographic delay line;
splitting an eluent from said first column into a first portion of eluent and a second portion of eluent;
providing at least one first device;
passing said first portion of eluent from said splitter to said first device such that a first part of said first portion of eluent arrives at said first device at a first time $t_1$ and a second part of said first portion of eluent arrives at said first device at a second time $t_2$;
passing said second portion of eluent from said splitter through said chromatographic delay line to said first device, such that the passage of said second portion of eluent from said splitter to said first device is delayed relative to the passage of said first portion of eluent from said splitter to said first device, and such that a first part of said second portion of eluent arrives at said first device at a third time $t_3$, where $t_1 < t_3 < t_2$;

analysing said first part of said first portion of eluent in a first mode of operation; and analysing said first part of said second portion of eluent in a second mode of operation.

* * * * *